US012751767B2

(12) United States Patent
Otto et al.

(10) Patent No.: US 12,751,767 B2
(45) **Date of Patent: *Oct. 6, 2026**

(54) SYSTEMS AND METHODS FOR GENERATING CUSTOMIZED CONTROL BOUNDARIES

(71) Applicant: MAKO Surgical Corp., Weston, FL (US)

(72) Inventors: Jason Otto, Plantation, FL (US); Hyosig Kang, Weston, FL (US)

(73) Assignee: MAKO SURGICAL CORP., Weston, FL (US)

( * ) Notice: Subject to any disclaimer, the term of this patent is extended or adjusted under 35 U.S.C. 154(b) by 360 days.

This patent is subject to a terminal disclaimer.

(21) Appl. No.: 18/497,581

(22) Filed: Oct. 30, 2023

(65) Prior Publication Data

US 2024/0058072 A1 Feb. 22, 2024

Related U.S. Application Data

(63) Continuation of application No. 17/483,999, filed on Sep. 24, 2021, now Pat. No. 11,832,887, which is a
(Continued)

(51) Int. Cl.
*A61B 34/10* (2016.01)
*A61B 6/00* (2006.01)
(Continued)

(52) U.S. Cl.
CPC ............ *A61B 34/10* (2016.02); *A61B 6/5211* (2013.01); *A61B 34/20* (2016.02); *A61B 34/30* (2016.02); *A61B 34/76* (2016.02); *G05B 15/02* (2013.01); *G06F 3/016* (2013.01); *G06T 7/0012* (2013.01); *G06T 7/13* (2017.01); *G06T 7/60* (2013.01); *G06T 15/00* (2013.01); *G16H 20/40* (2018.01); *G16H 30/20* (2018.01); *G16H 50/50* (2018.01);
(Continued)

(58) Field of Classification Search
CPC ......... A61B 34/10; A61B 34/20; A61B 34/30; A61B 34/76
USPC .................................................... 606/1, 86 R
See application file for complete search history.

(56) References Cited

U.S. PATENT DOCUMENTS

D622,854 S 8/2010 Otto et al.
D625,415 S 10/2010 Otto et al.
(Continued)

FOREIGN PATENT DOCUMENTS

CN 101160104 A 4/2008
CN 102281831 A 12/2011
(Continued)

OTHER PUBLICATIONS

U.S. Appl. No. 29/329,712, filed Dec. 19, 2008, Otto.
(Continued)

*Primary Examiner* — Jessica Weiss
(74) *Attorney, Agent, or Firm* — Foley & Lardner LLP

(57) ABSTRACT

A method includes providing a boundary defining a portion of a bone to be resected, determining a position of a tracked probe, obtaining a customized boundary by changing a shape of the boundary based on the position of the tracked probe, and guiding operation of a cutting tool in an area defined by the customized boundary.

20 Claims, 11 Drawing Sheets

Related U.S. Application Data continuation of application No. 15/451,105, filed on Mar. 6, 2017, now Pat. No. 11,160,609, which is a continuation of application No. 14/578,064, filed on Dec. 19, 2014, now Pat. No. 9,588,587.

(60) Provisional application No. 61/922,740, filed on Dec. 31, 2013.

(51) Int. Cl.

| | |
|---|---|
| ***A61B 34/00*** | (2016.01) |
| ***A61B 34/20*** | (2016.01) |
| ***A61B 34/30*** | (2016.01) |
| ***G05B 15/02*** | (2006.01) |
| ***G06F 3/01*** | (2006.01) |
| ***G06T 7/00*** | (2017.01) |
| ***G06T 7/13*** | (2017.01) |
| ***G06T 7/60*** | (2017.01) |
| ***G06T 15/00*** | (2011.01) |
| ***G16H 20/40*** | (2018.01) |
| ***G16H 30/20*** | (2018.01) |
| ***G16H 50/50*** | (2018.01) |
| *A61B 90/00* | (2016.01) |

(52) U.S. Cl.

CPC ... *A61B 2034/102* (2016.02); *A61B 2034/104* (2016.02); *A61B 2034/105* (2016.02); *A61B 90/03* (2016.02); *G06T 2200/24* (2013.01); *G06T 2207/10081* (2013.01); *G06T 2207/30004* (2013.01)

(56) References Cited

U.S. PATENT DOCUMENTS

| | | | | |
|---|---|---|---|---|
| D626,234 | S | 10/2010 | Otto et al. | |
| 7,842,092 | B2 | 11/2010 | Otto et al. | |
| 8,010,180 | B2 | 8/2011 | Quaid et al. | |
| 8,475,535 | B2 | 7/2013 | Otto | |
| 8,543,234 | B2 | 9/2013 | Gao | |
| 8,702,803 | B2 | 4/2014 | Otto et al. | |
| 8,717,430 | B2 | 5/2014 | Simon et al. | |
| 8,911,501 | B2 | 12/2014 | Rwin et al. | |
| 8,977,021 | B2 | 3/2015 | Kang et al. | |
| 9,061,160 | B2 | 6/2015 | Stone et al. | |
| D744,103 | S | 11/2015 | Irwin et al. | |
| D744,104 | S | 11/2015 | Bechtold et al. | |
| D745,158 | S | 12/2015 | Irwin et al. | |
| 9,275,192 | B2 | 3/2016 | Kang et al. | |
| 9,292,657 | B2 | 3/2016 | Kang et al. | |
| 9,724,109 | B2 | 8/2017 | Nadzadi et al. | |
| 2006/0142657 | A1 * | 6/2006 | Quaid | A61B 90/37 600/424 |
| 2008/0058945 | A1 | 3/2008 | Hajaj et al. | |
| 2008/0262812 | A1 | 10/2008 | Arata et al. | |
| 2009/0000626 | A1 | 1/2009 | Quaid et al. | |
| 2009/0000627 | A1 | 1/2009 | Quaid et al. | |
| 2009/0012531 | A1 | 1/2009 | Quaid et al. | |
| 2009/0012532 | A1 | 1/2009 | Quaid et al. | |
| 2009/0287467 | A1 | 11/2009 | Sparks et al. | |
| 2010/0094429 | A1 | 4/2010 | Otto | |
| 2010/0153076 | A1 | 6/2010 | Bellettre et al. | |
| 2010/0153081 | A1 * | 6/2010 | Bellettre | G06T 17/20 715/764 |
| 2010/0170362 | A1 | 7/2010 | Bennett et al. | |
| 2010/0217400 | A1 | 8/2010 | Nortman et al. | |
| 2011/0066079 | A1 | 3/2011 | Otto et al. | |
| 2011/0082468 | A1 | 4/2011 | Hagag et al. | |
| 2011/0092804 | A1 | 4/2011 | Schoenefeld et al. | |
| 2011/0257653 | A1 | 10/2011 | Hughes et al. | |
| 2011/0282473 | A1 | 11/2011 | Pavlovskaia et al. | |
| 2012/0109150 | A1 | 5/2012 | Quaid et al. | |
| 2012/0310617 | A1 | 12/2012 | Bellettre et al. | |
| 2013/0144135 | A1 * | 6/2013 | Mahfouz | G06T 19/20 600/309 |
| 2013/0172783 | A1 | 7/2013 | Ikits et al. | |
| 2013/0173008 | A1 | 7/2013 | Bechtold et al. | |
| 2013/0197687 | A1 | 8/2013 | Pavlovskaia et al. | |
| 2013/0211792 | A1 | 8/2013 | Kang et al. | |
| 2014/0180290 | A1 | 6/2014 | Otto et al. | |
| 2014/0188134 | A1 | 7/2014 | Nortman et al. | |
| 2014/0189508 | A1 | 7/2014 | Granchi et al. | |
| 2015/0182343 | A1 | 7/2015 | Nadzadi et al. | |
| 2022/0008132 | A1 | 1/2022 | Otto et al. | |

FOREIGN PATENT DOCUMENTS

| | | | | |
|---|---|---|---|---|
| CN | 102300515 | A | 12/2011 | |
| CN | 102612350 | A | 7/2012 | |
| JP | 2009-537231 | A | 10/2009 | |
| WO | WO-2006/091494 | A1 | 8/2006 | |
| WO | WO-2006106419 | A2 * | 10/2006 | A61B 17/155 |
| WO | WO-2010/068212 | | 6/2010 | |
| WO | WO-2013/101753 | A1 | 7/2013 | |

OTHER PUBLICATIONS

U.S. Appl. No. 29/329,715, filed Dec. 19, 2008, Otto.

International Search Report and Written Opinion for PCT Application No. PCT/US2014/071680, dated Mar. 25, 2015, 9 pages.

* cited by examiner

SYSTEMS AND METHODS FOR GENERATING CUSTOMIZED CONTROL BOUNDARIES

CROSS-REFERENCE TO RELATED APPLICATIONS

This application is a continuation of U.S. application Ser. No. 17/483,999, filed Sep. 24, 2021, which is a continuation of U.S. application Ser. No. 15/451,105, filed Mar. 6, 2017, which is a continuation of U.S. application Ser. No. 14/578,064, filed Dec. 19, 2014, which claims the benefit of and priority to U.S. Provisional Application No. 61/922,740, filed Dec. 31, 2013, all of which are incorporated herein by reference in their entireties.

BACKGROUND

The present disclosure relates generally to force feedback systems associated with computer-assisted surgery ("CAS") systems and, more particularly, to systems and methods for customizing interactive haptic boundaries associated with CAS systems based on patient-specific information.

The knee joint comprises the interface between the distal end of the femur and the proximal end of the tibia. In a properly-functioning knee joint, medial and lateral condyles of the femur pivot smoothly along menisci attached to respective medial and lateral condyles of the tibia. When the knee joint is damaged, the natural bones and cartilage that form the joint may be unable to properly articulate, which can lead to joint pain and, in some cases, interfere with normal use of the joint.

In some situations, surgery is required to restore normal use of the joint and reduce pain. Depending upon the severity of the damage, the surgery may involve partially or completely replacing the joint with prosthetic components. During such knee replacement procedures, a surgeon resects damaged portions of the bone and cartilage, while attempting to leave healthy tissue intact. The surgeon then fits the healthy tissue with artificial prosthetic components designed to replicate the resected tissue and restore proper knee joint operation.

Typically, prior to the surgery, the surgeon develops a preliminary ("pre-operative") plan that serves as a guide to performing the surgery. As part of the pre-operative planning, the surgeon surveys, among other things, the size, shape, kinematic function, and condition of the patient's joint. Using computer-assisted surgery systems, this survey can be performed by obtaining computer-based images of the joint and generating a computer-based model of the joint of the patient in virtual software space. Using this virtual model, the surgeon can evaluate the condition of the anatomic features of the joint and plan, among other things, the location and amount of bone that needs to be removed and the position and orientation in which the prosthetic components should be implanted on the bone to restore normal joint functionality.

Although the surgeon has a great degree of flexibility in customizing most aspects of the surgery based on the unique anatomy of the patient, the surgeon is typically limited to selecting from among a finite number of different prosthetic implant components. In many situations, a surgeon performs surgery on a patient whose anatomy does not precisely match any of the available prosthetic implant components. As a result, the surgeon may select a prosthetic implant that most closely fits—but does not precisely match—the patient's anatomy. The surgeon can then modify the surgical plan (either pre or intra-operatively) to accommodate for the selected prosthetic components.

In some situations, the CAS system may include a force feedback control system that is coupled to one or more surgical instruments (e.g., cutting tools) and configured to provide force feedback for controlling the surgical instrument during the surgery. The force feedback control system may constrain the cutting tool to limit the position or operation of the surgical instrument to within certain predefined boundaries. By allowing users to strategically define the placement of the virtual boundaries associated with the force feedback control system, these CAS systems enable surgeons to precisely and accurately control the resection and sculpting of the bone in preparation for receiving the prosthetic implant.

Because CAS systems provide a solution for accurately, reliably, and precisely executing bone cuts by defining the boundaries at which a cutting surface of a surgical instrument can operate, some CAS systems now include virtual software models that match the size and shape of available prosthetic implants. The virtual software model of the implant(s) can be positioned (in software) relative to the virtual model(s) of the patient's joint prior to or during the surgical procedure. Once positioned, the software model of the implant may be "registered" to the virtual model of the patient's anatomy so that the cutting surface is constrained to operate only within the area defined by the software model of the implant, limiting tissue removal only to the specific area of the patient's bone associated with the registered placement of the implant.

Systems that provide virtual models, and corresponding haptic boundaries, associated with a selection of available implants may allow surgeons to quickly and efficiently define a resection pattern for preparing the bone to receive the implant. Generally, each virtual implant model may be associated with a corresponding fixed haptic boundary, which may be based on the size and shape to the geometry associated with the virtual implant model. However, in some situations the surgeon selects an undersized prosthetic implant, but nonetheless wishes to remove areas of diseased or damaged tissue that may be located beyond the boundaries required to accommodate the undersized prosthetic implant.

SUMMARY

In accordance with one aspect, the present disclosure is directed to a method for customizing a haptic boundary based on a patient-specific anatomy. The method may include identifying a standard haptic boundary based on a geometry of a virtual implant model to be implanted on the anatomy. The method may also include identifying a reference feature associated with a virtual implant model and determining an intersection between the identified reference feature and a virtual model associated with an anatomy of the patient. An anatomic perimeter at the intersection between the identified reference feature and the virtual model of the anatomy may be identified and at least one anatomic feature may be determined on the virtual model of the anatomy. The standard haptic boundary may be modified based on the at least one anatomic feature to generate a customized haptic boundary.

According to another aspect, the present disclosure is directed to another method for method for customizing a haptic boundary based on a patient-specific anatomy. The method may include displaying a graphical representation of an implant in virtual coordinate space and displaying a graphical representation of a bone in the virtual coordinate space. The method may further include positioning the graphical representation of the implant relative to the graphical representation of the bone based on a user input. The method may also include displaying a graphical representation of a standard haptic boundary based on the geometry of the implant and extracting reference feature information associated with the graphical representation of the implant. An anatomic perimeter at an intersection between the extracted reference feature and the graphical representation of the bone may be mapped, and at least one anatomic feature on the graphical representation of the bone from the intersection of the reference feature and the graphical representation of the bone may also be mapped. The method may further include modifying the standard haptic boundary based on at least one anatomic feature to generate a customized haptic boundary, and displaying a graphical representation of the customized haptic boundary in the virtual coordinate space.

In accordance with yet another aspect, the present disclosure is directed to a computer-assisted surgery system including a display, an input device configured to receive data input by a user, and a processor operatively coupled to the input device and the display. The processor may be configured to identify a standard haptic boundary based on a geometry of a virtual implant model to be implanted on the anatomy, identify a reference feature associated with a virtual implant model, and determine an intersection between the identified reference feature and a virtual model associated with an anatomy of the patient. The processor may also be configured to identify an anatomic perimeter at the intersection between the identified reference feature and the virtual model of the anatomy and determine at least one anatomic feature on the virtual model of the anatomy from the intersection of the reference feature and the virtual model of the anatomy. The processor may also be configured to modify the standard haptic boundary based on at least one anatomic feature to generate a customized haptic boundary, and display the customized haptic boundary and the virtual model associated with the anatomy of the patient on the display.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments that, together with the description, serve to explain the principles and features of the present disclosure.

DETAILED DESCRIPTION

Reference will now be made in detail to exemplary embodiments of the present disclosure, examples of which are illustrated in the accompanying drawings.

A healthy knee joint comprises the interface between the distal end of the femur and the proximal end of the tibia. If the healthy knee joint becomes damaged due, for example, to injury or disease, knee surgery may be required to restore normal structure and function of the joint. If the damage to the knee is severe, total knee arthroplasty ("TKA") may be required. TKA typically involves the removal of the damaged portion of joint and the replacement of the damaged portion of the joint with one or more prosthetic components.

In some TKA procedures, one or more of cruciate ligaments (including anterior cruciate ligament and/or posterior cruciate ligament) may be left intact, to be re-used with the prosthetic implants to form the new knee joint. In these "cruciate-retaining" applications, the prosthetic implant components may be configured to avoid interference with or impingement on the retained cruciate ligaments passing through the intercondylar area of the knee joint. For example, each of the femoral and tibial prosthetic components may be designed with a intercondylar "notch" that extends from the posterior of the prosthetic component toward the anterior of the prosthetic component. The femoral and tibial intercondylar notches provide a passage that allows the cruciate ligament to pass from the femoral intercondylar fossa down to the tibial eminence.

Because cruciate ligaments are exposed to significant tensile force during normal knee joint use, it is important that the attachment sites where the cruciate ligaments attach to the femur and tibia have sufficient strength to properly anchor the cruciate ligaments to the bone. Otherwise, the force applied by the cruciate ligament strains the tissue around the attachment site, possibly leading to failure of the joint, which may require corrective surgery to repair. One way to limit the possibility of such a failure is to limit the amount of bone resected at or near the attachment site(s) (i.e., the intercondylar fossa of the femur and tibial emmence 101*a* of the tibia). Limiting the amount of disturbance of native tissue at the attachment sites helps preserve the natural anchoring mechanism of the tissue, which decreases the likelihood of failure at the attachment site.

Figure 1:
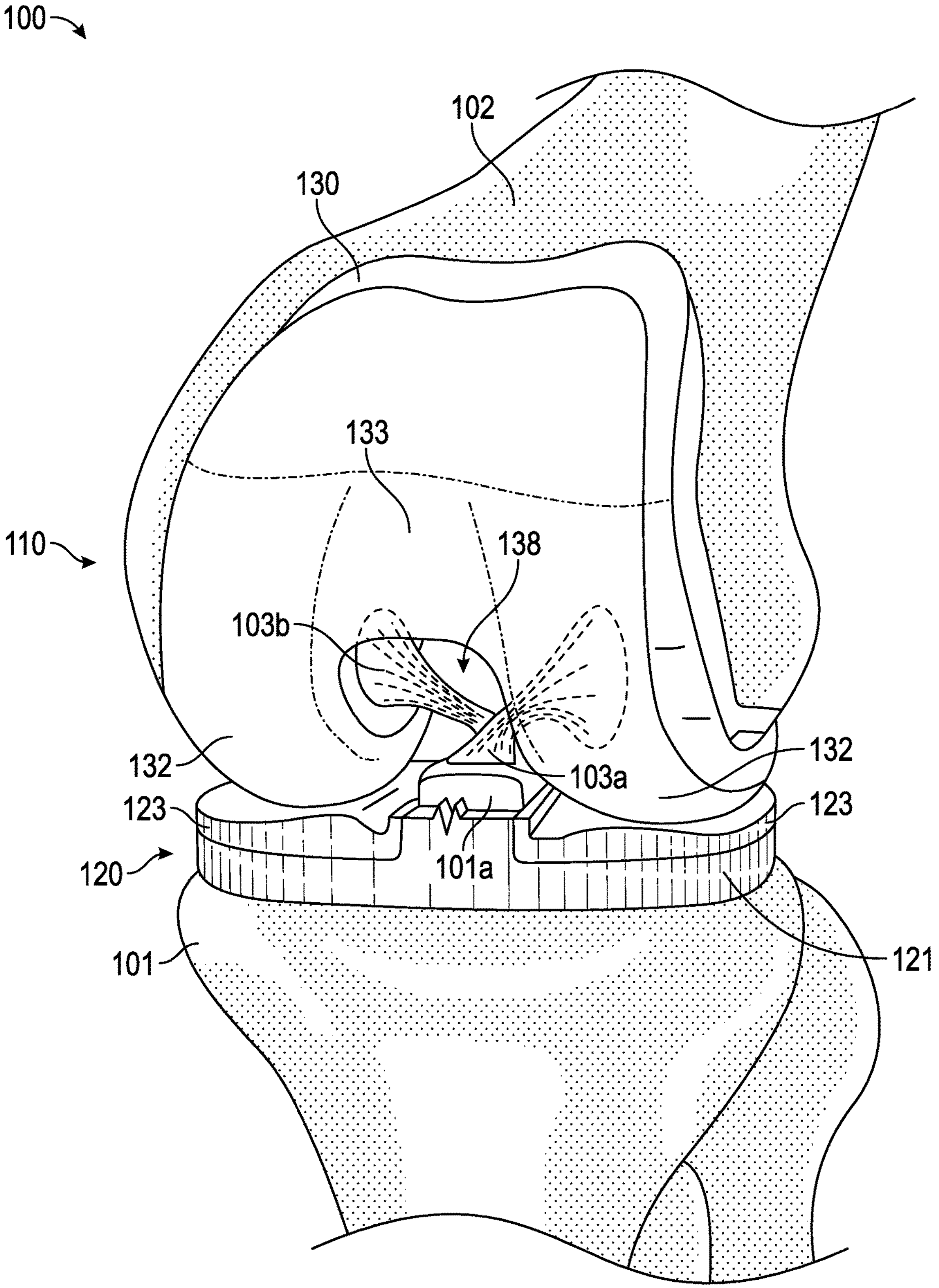
FIG. 1 illustrates a perspective view of post-operative prosthetic knee joint fitted with a prosthetic system.

In the embodiment illustrated in FIG. 1, prosthetic implant system 110 includes a number of components configured to replace a resected portion of a native knee joint. According to one embodiment, prosthetic implant system 110 includes a tibial implant system 120 configured to replace a resected portion of a native tibia 101. Prosthetic implant system 110 also includes a femoral component 130 configured to replace a resected portion of a native femur 102. After implantation during knee replacement surgery, tibial implant system 120 and femoral component 130 cooperate to replicate the form and function of the native knee joint.

Femoral component 130 is secured to the distal end of femur 102 and configured to replace the structure and function of the native femoral portion of knee joint 100. As such, femoral component 130 may be manufactured from surgical-grade metal or metal alloy material (such as surgical-grade steel, titanium or titanium allow, a cobalt-chromium alloy, a zirconium alloy, or tantalum) that is substantially rigid for providing sufficient strength to support the forces required of the knee joint. According to one embodiment, femoral component 130 may embody a single component having a plurality of different structural features, each configured to perform a particular function associated with the knee joint 100. For example, femoral component 130 may include a pair of condyles 132, each of which is coupled to a patellar guide portion 133. The pair of condyles 132 are separated from one another by an intercondylar notch 138, which provides a channel through which one or more cruciate ligaments 103, such as anterior cruciate ligament (ACL) 103*a* and/or posterior cruciate ligament (PCL) 103*b*, may pass.

Tibial implant system 120 may include a plurality of components that cooperate to provide a stable surface that articulates with femoral component 130 to restore proper knee joint function. As illustrated in FIG. 1, tibial implant system 120 includes a base portion 121 and one or more insert portions 123. During a knee replacement procedure, base portion 121 is secured to the proximal end of the tibia 101, which has been surgically prepared by removing damaged bone and tissue and reshaping the healthy bone to receive the base portion 121. Once base portion 121 is secured to tibia 101, the surgeon completes assembly of tibial implant system 120 by engaging and securing insert portions 123 within base portion 121. Base portion 121 of tibial prosthetic system may be configured with a passage through the center to allow for connection between the retained cruciate ligaments 103 and tibial eminence 101*a*.

Base portion 121 may be configured to emulate the structure and function of the top surface of tibia 101. Thus, similar to femoral component 130, base portion 121 may be manufactured from surgical-grade metal or metal alloy material (such as surgical-grade steel, titanium or titanium allow, a cobalt-chromium alloy, a zirconium alloy, or tantalum) that is substantially rigid for providing a stable base upon which to reconstruct the remainder of the prosthetic joint.

Insert portions 123 may be designed to emulate the form and function of certain components of the natural femorotibial interface, including, among other things, medial and lateral menisci of the knee joint. As such, insert portions 123 may be constructed of smooth, semi-rigid synthetic or semi-synthetic plastic, rubber, or polymer material. Insert portions 123 may be configured to provide a smooth surface that is designed to articulate with a femoral component 130 during normal knee operation. According to one embodiment, insert portions 123 are configured to removably engage with base portion 121. Accordingly, insert portions 123 are configured for periodic replacement if insert portions 123 deteriorate over time due, for example, to excessive wear.

In order to ensure precise and accurate preparation of the joint to receive a prosthetic implant, CAS system may be used to generate a graphical representation of the surgical site and a corresponding virtual guide that may aid the surgeon in properly aligning the tool prior to interaction with patient's anatomy. Many CAS systems include software that allows users to electronically register certain anatomic features (e.g., bones, soft tissues, etc.), surgical instruments, and other landmarks associated with the surgical site. CAS systems may generate a graphical representation of the surgical site based on the registration of the anatomic features. The CAS software also allows users to plan certain aspects of the surgical procedure, and register these aspects for display with the graphical representation of the surgical site. For example, in a knee joint replacement procedure, a surgeon may register target navigation points, the location and depth of bone and tissue cuts, virtual boundaries that may be associated with a corresponding reference for the application of haptic force, and other aspects of the surgery.

Figure 2:
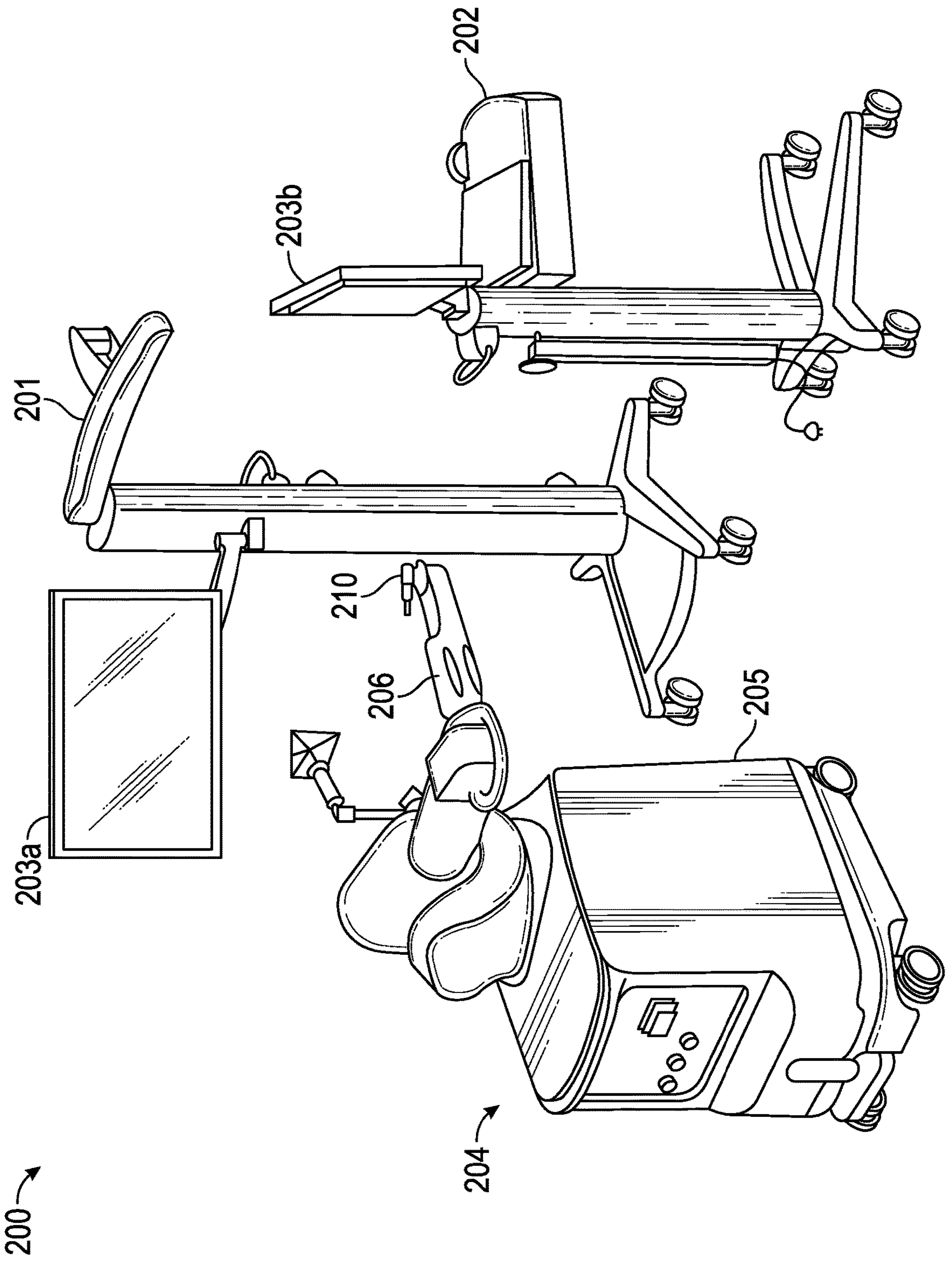
FIG. 2 provides a schematic illustration of an exemplary computer-assisted surgery (CAS) system, in which certain methods consistent with the disclosed embodiments may be implemented.

FIG. 2 provides a schematic diagram of an exemplary computer-assisted surgery (CAS) system 200, in which processes and features associated with certain disclosed embodiments may be implemented. CAS system 200 may be configured to perform a wide variety of orthopedic surgical procedures such as, for example, partial or total joint replacement surgeries. As illustrated in FIG. 2, CAS system 200 includes a tracking system 201, computer-assisted navigation system 202, one or more display devices 203*a*, 203*b*, and a robotic system 204. It should be appreciated that CAS system 200, as well as the methods and processes described herein, may be applicable to many different types of joint replacement procedures. Although certain disclosed embodiments may be described with respect to knee replacement procedures, the concepts and methods described herein may be applicable to other types of orthopedic surgeries, such as partial hip replacement, full or partial hip resurfacing, shoulder replacement or resurfacing procedures, and other types of orthopedic procedures.

Robotic system 204 can be used in an interactive manner by a surgeon to perform a surgical procedure, such as a knee replacement procedure, on a patient. As shown in FIG. 2, robotic system 204 includes a base 205, an articulated arm 206, a force system (not shown), and a controller (not shown). A surgical tool 210 (e.g., an end effector having an operating member, such as a saw, reamer, or burr) may be coupled to the articulated arm 206. The surgeon can manipulate the surgical tool 210 by grasping and manually moving the articulated arm 206 and/or the surgical tool 210.

The force system and controller are configured to provide control or guidance to the surgeon during manipulation of the surgical tool. The force system is configured to provide at least some force to the surgical tool via the articulated arm 206, and the controller is programmed to generate control signals for controlling the force system. In one embodiment, the force system includes actuators and a backdriveable transmission that provide haptic (or force) feedback to constrain or inhibit the surgeon from manually moving the surgical tool beyond predefined virtual boundaries defined by haptic objects as described, for example, in U.S. Pat. No. 8,010,180 and/or U.S. patent application Ser. No. 12/654,519 (U.S. Patent Application Pub. No. 2010/0170362), filed Dec. 22, 2009, each of which is hereby incorporated by reference herein in its entirety. According to one embodiment, CAS system 200 is the RIO® Robotic Arm Interactive Orthopedic System manufactured by MAKO Surgical Corp. of Fort Lauderdale, Florida. The force system and controller may be housed within the robotic system 204.

Tracking system 201 may include any suitable device or system configured to track the relative locations, positions, orientations, and/or poses of the surgical tool 210 (coupled to robotic system 204) and/or positions of registered portions of a patient's anatomy, such as bones. Such devices may employ optical, mechanical, or electromagnetic pose tracking technologies. According to one embodiment, tracking system 201 includes a vision-based pose tracking technology, wherein an optical detector, such as a camera or infrared sensor, is configured to determine the position of one or more optical transponders (not shown). Based on the position of the optical transponders, tracking system 201 may capture the pose (i.e., the position and orientation) information of a portion of the patient's anatomy that is registered to that transponder or set of transponders.

Navigation system 202 may be communicatively coupled to tracking system 201 and may be configured to receive tracking data from tracking system 201. Based on the received tracking data, navigation system 202 may determine the position and orientation associated with one or more registered features of the surgical environment, such as surgical tool 210 or portions of the patient's anatomy. Navigation system 202 may also include surgical planning and surgical assistance software that may be used by a surgeon or surgical support staff during the surgical procedure. For example, during a joint replacement procedure, navigation system 202 may display images related to the surgical procedure on one or both of the display devices 203*a*, 203*b*.

Figure 3:
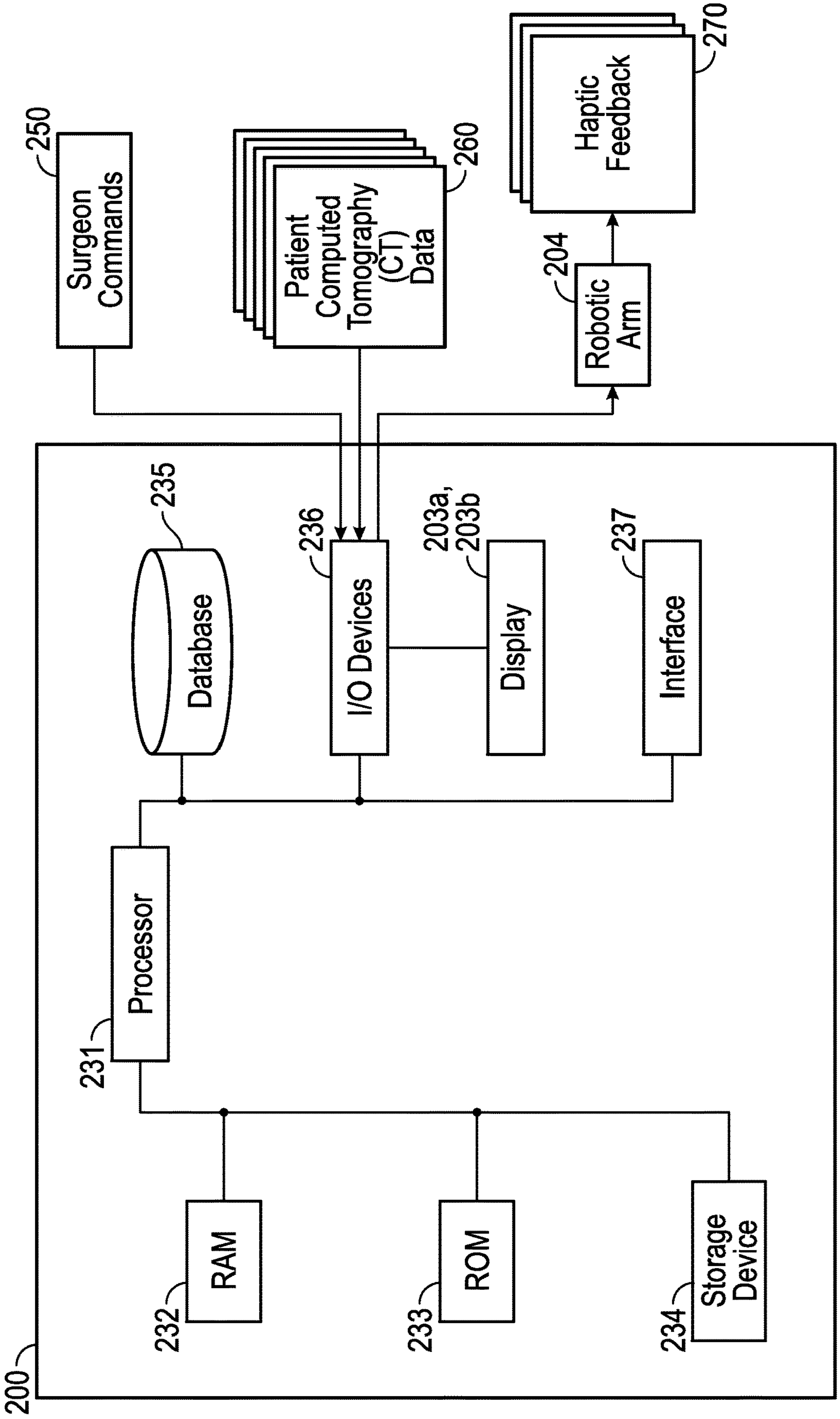
FIG. 3 provides a schematic diagram of an exemplary computer system, which may be used in one or more components associated with the CAS system illustrated in FIG. 2.

Navigation system 202 (and/or one or more constituent components of CAS system 200) may include or embody a processor-based system (such as a general or special-purpose computer) in which processes and methods consistent with the disclosed embodiments may be implemented. For example, as illustrated in FIG. 3, CAS system 200 may include one or more hardware and/or software components configured to execute software programs, such as, tracking software, surgical navigation software, 3-D bone modeling or imaging software, and/or software for establishing and modifying virtual haptic boundaries for use with a force system to provide haptic feedback to surgical tool 210. For example, CAS system 200 may include one or more hardware components such as, for example, a central processing unit (CPU) (processor 231); computer-readable media, such as a random access memory (RAM) module 232, a read-only memory (ROM) module 233, and a storage device 234; a database 235; one or more input/output (I/O) devices 236; and a network interface 237. The computer system associated with CAS system 200 may include additional, fewer, and/or different components than those listed above. It is understood that the components listed above are exemplary only and not intended to be limiting.

Processor 231 may include one or more microprocessors, each configured to execute instructions and process data to perform one or more functions associated with CAS system 200. As illustrated in FIG. 3, processor 231 may be communicatively coupled to RAM 232, ROM 233, storage device 234, database 235, I/O devices 236, and network interface 237. Processor 231 may be configured to execute sequences of computer program instructions to perform various processes, which will be described in detail below. The computer program instructions may be loaded into RAM for execution by processor 231.

Computer-readable media, such as RAM 232, ROM 233, and storage device 234, may be configured to store computer-readable instructions that, when executed by processor 231, may cause CAS system 200 or one or more constituent components, such as navigation system 202, to perform functions or tasks associated with CAS system 200. For example, computer readable media may include instructions for causing the CAS system 200 to perform one or more methods for determining changes in parameters of a knee joint after a knee arthroplasty procedure. Computer-readable media may also contain instructions that cause tracking system 201 to capture positions of a plurality of anatomic landmarks associated with certain registered objects, such as surgical tool 210 or portions of a patient's anatomy, and cause navigation system 202 to generate virtual representations of the registered objects for display on I/O devices 236. Exemplary methods for which computer-readable media may contain instructions will be described in greater detail below. It is contemplated that each portion of a method described herein may have corresponding instructions stored in computer-readable media for causing one or more components of CAS system 200 to perform the method described.

I/O devices 236 may include one or more components configured to communicate information with a user associated with CAS system 200. For example, I/O devices 236 may include a console with an integrated keyboard and mouse to allow a user (e.g., a surgeon) to input parameters (e.g., surgeon commands 250) associated with CAS system 200. I/O devices 236 may also include a display, such as monitors 203*a*, 203*b*, including a graphical user interface (GUI) for outputting information on a monitor. I/O devices 236 may also include peripheral devices such as, for example, a printer for printing information associated with CAS system 200, a user-accessible disk drive (e.g., a USB port, a floppy, CD-ROM, or DVD-ROM drive, etc.) to allow a user to input data stored on a portable media device, a microphone, a speaker system, or any other suitable type of interface device. For example, I/O devices 236 may include an electronic interface that allows a user to input patient computed tomography (CT) data 260 into CAS system 200. This CT data may then be used to generate and manipulate virtual representations of portions of the patient's anatomy (e.g., a virtual model of a tibia 101) in software.

Software associated with CAS system 200 may be configured to enable surgical planning, navigation, and basic image guided surgery capabilities. For example, software associated with CAS system 200 may include computer-implemented processes for generating and displaying images (either captured images or computer-generated captured images) from image data sets, computer-implemented processes for determining a position of a tip and an orientation of an axis of a surgical instrument, and computer-implemented processes for registering a patient and an image data set to a coordinate frame of the tracking system 201. These processes may enable, for example, the CAS system 200 to display on the display device(s) 203*a*, 203*b* a virtual representation of a tracked surgical instrument (and/or a prosthetic implant) overlaid on one or more images of a patient's anatomy and to update the virtual representation of the tracked instrument in real-time during a surgical procedure. Images generated from the image data set may be two-dimensional or, in the case of a three-dimensional image data set, a three-dimensional reconstruction based, for example, on segmentation of the image data set. According to one embodiment, images associated with the image data set may include CT scan data associated with a patient's anatomy, a prosthetic implant, or any object. When more than one image is shown on the display device(s) 203*a*, 203*b*, the CAS system 200 may coordinate the representation of the tracked instrument among the different images.

According to another embodiment, an imageless system may be utilized to generate and manipulate virtual representations of portions of the patient's anatomy (e.g., a virtual model of a tibia 101) in software. Imageless systems include technologies that are well-known in the art, such as systems utilizing statistically shaped models and methods of bone morphing. In one form of imageless system, a virtual representation of a portion of the patient's anatomy is created based on patient-specific characteristics (such as anatomic landmarks obtained by physically touching the patient's anatomy using a probe tool). In other imageless systems, a three-dimensional virtual representation of a portion of the patient's anatomy is obtained by selecting a three-dimensional model from a database or library of bone models. The selected bone model can then be deformed based on patient-specific characteristics, creating a three-dimensional representation of the patient's anatomy.

Processor 231 associated with CAS system 200 may be configured to establish a virtual haptic geometry associated with or relative to one or more features of a patient's anatomy. As explained, CAS system 200 may be configured to create a virtual representation of a surgical site that includes, for example, virtual representations of a patient's anatomy, a surgical instrument to be used during a surgical procedure, a probe tool for registering other objects within the surgical site, and any other such object associated with a surgical site.

In addition to physical objects, CAS system 200 may be configured to generate virtual objects that exist in software and may be useful during the performance of a surgical procedure. For example, CAS system 200 may be configured to generate virtual boundaries that correspond to a surgeon's plan for preparing a bone, such as boundaries defining areas of the bone that the surgeon plans to cut, remove, or otherwise alter. Alternatively or additionally, CAS system 200 may define virtual objects that correspond to a desired path or course over which a portion of surgical tool 210 should navigate to perform a particular task.

Virtual boundaries and other virtual objects may define a point, line, or surface within a virtual coordinate space (typically defined relative to an anatomy of a patient) that serves as a boundary at which haptic feedback is provided to a surgical instrument when the tracked position of the surgical instrument interacts with the virtual boundary or object. For example, as the surgeon performs a bone cutting operation, tracking system 201 of CAS system 200 tracks the location of the cutting tool and allows the surgeon to freely move the tool in the workspace while the virtual representation of the cutting tool is not proximate to the haptic boundary. However, when the representation of the tool is in proximity to a virtual haptic boundary (that has been registered to the anatomy of the patient), CAS system 200 controls the force feedback system to provide haptic guidance that tends to constrain the surgeon from penetrating the virtual haptic boundary with the cutting tool. For example, a virtual haptic boundary may be associated with the geometry of a virtual model of a prosthetic implant, and the haptic guidance may comprise a force and/or torque that is mapped to the virtual boundary and experienced by the surgeon as resistance to constrain tool movement from penetrating the virtual boundary. Thus, the surgeon may feel as if the cutting tool has encountered a physical object, such as a wall. In this manner, the virtual boundary functions as a virtual cutting guide. Accordingly, the force feedback system of CAS system 200 communicates information to the surgeon regarding the location of the tool relative to the virtual boundary, and provides physical force feedback to guide the cutting tool during the actual cutting process. The force feedback system of CAS system 200 may also be configured to limit the user's ability to manipulate the surgical tool.

Figure 4:
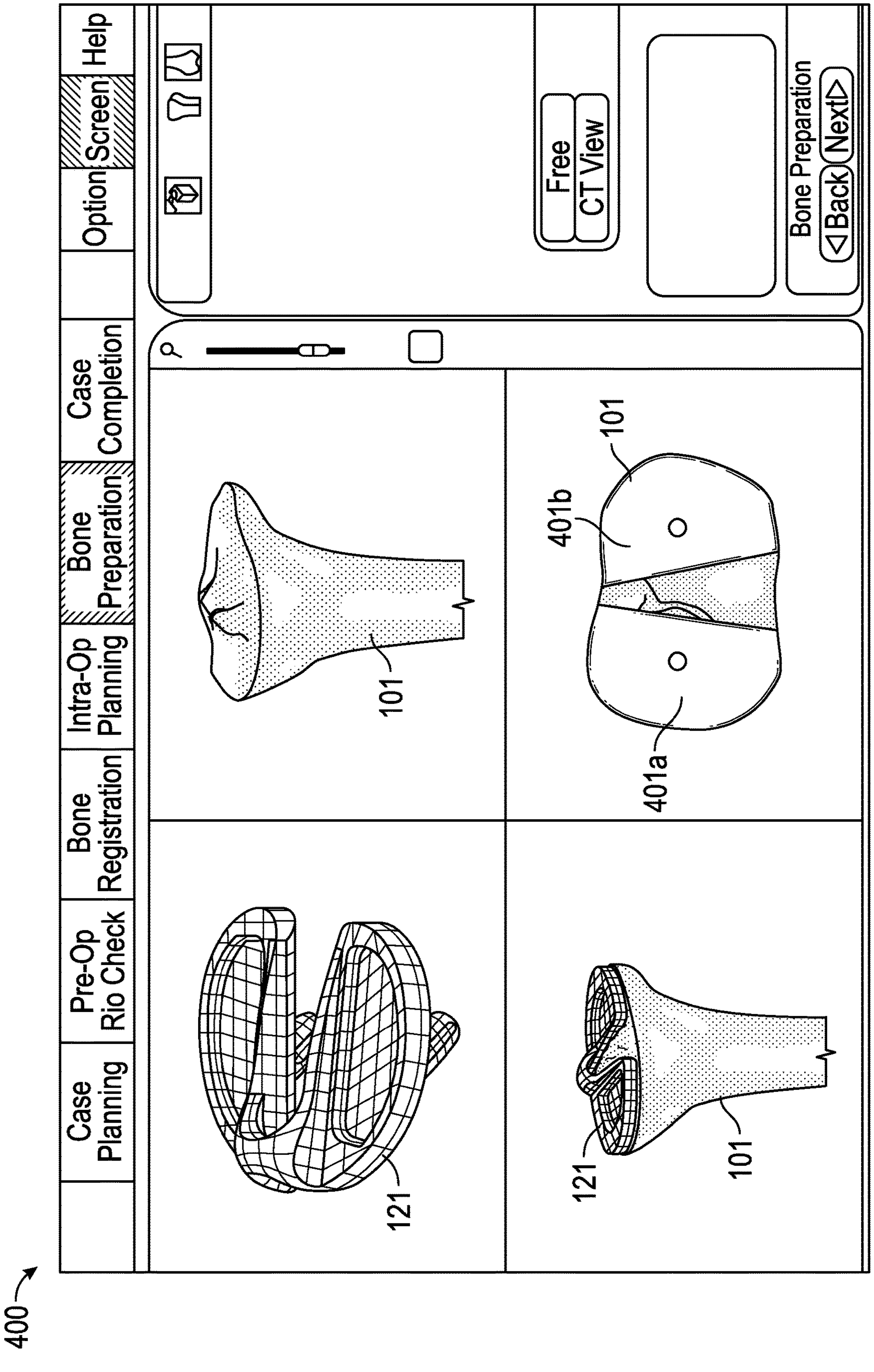
FIG. 4 illustrates an exemplary screen shot associated with a graphical user interface of the CAS system, in accordance with certain disclosed embodiments.

Systems and methods consistent with the disclosed embodiments provide a solution for customizing a virtual haptic boundary and providing a haptic feedback for guiding the surgical instrument. According to one embodiment, the virtual haptic boundary may be customized based on a user request to modify a default boundary associated with a corresponding implant geometry. Alternatively or additionally, the virtual haptic boundary may be customized based, at least in part, on a detection of the patient's anatomy (e.g., a location of soft tissue, the edge perimeter of a bone, etc.). The process for customizing the virtual haptic boundary may be part of an implant planning phase, during which the surgeon pre-operatively or intra-operatively plans the placement of prosthetic implants and the corresponding modification/removal of joint tissue to accommodate the implant. FIG. 4 provides an exemplary screen shot of a graphical user interface associated with planning software for CAS system 200.

FIG. 4 illustrates an exemplary screen shot 400 associated with a graphical user interface screen of planning software associated with CAS system 200. As illustrated in FIG. 4, planning software may include virtual models of prosthetic implants, such as a tibial base portion 121 associated with tibial implant system 120. According to one embodiment, a virtual implant model may be provided by the manufacturer of the prosthetic implant and may provide a graphical representation of the geometry of the prosthetic implant. Using the graphical representation of the geometry, a virtual haptic boundary may be created and associated with the virtual implant model.

The graphical user interface 400 may include a plurality of sub-screens, each of which is configured to display a particular feature of the implant planning. For example, graphical user interface 400 may include a first sub-screen (e.g., upper left) for displaying the selected virtual implant model (e.g., a model associated with tibia base portion 121). Graphical user interface 400 may include a second sub-screen (upper right) for displaying the virtual model associated with the patient's anatomy (e.g., tibia 101) upon which the implant will be positioned. Graphical user interface 400 may include a third sub-screen (lower left) for displaying the planned placement of virtual implant model within the patient's anatomy. Graphical user interface 400 may also include a fourth sub-screen (lower right) for displaying a view of respective medial and lateral resection portions 401*a*, 401*b* associated with the planned implant placement. It is contemplated that the number and view of sub-screens may differ from those provided in the exemplary embodiment illustrated in FIG. 4. It is also contemplated that one or more of the sub-screens allow a user to interactively update the view and/or the components within the view. For example, although the lower right screen shows a top view of the simulated resection of the patient's tibia 101 based on the planned implant placement shown in the lower left sub-screen, it is contemplated that the user can select different views (e.g., front, back, side, bottom, etc.) for displaying the contents of the sub-screen.

Figure 5:
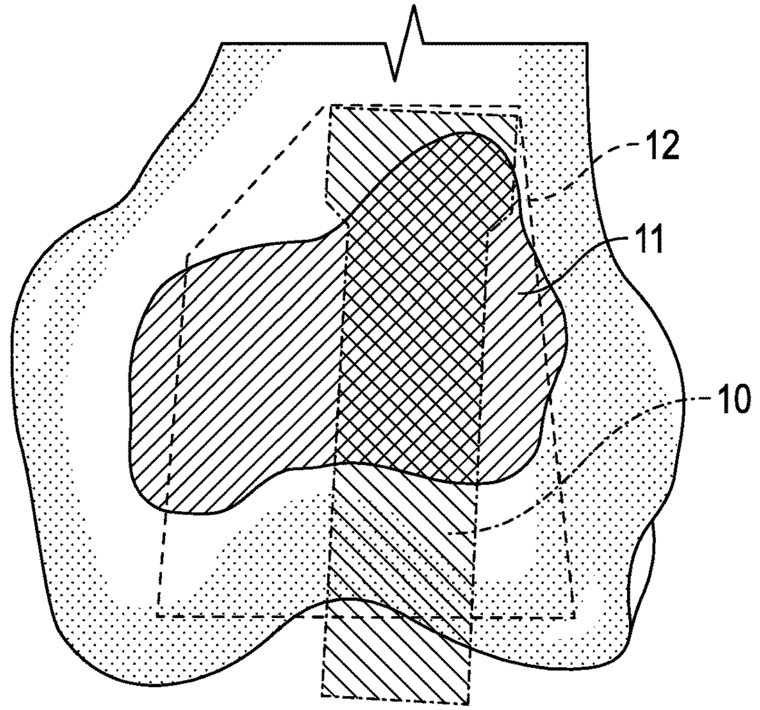
FIG. 5 illustrates a virtual representation of a standard haptic boundary for a tibial prosthetic component.
Figure 6:
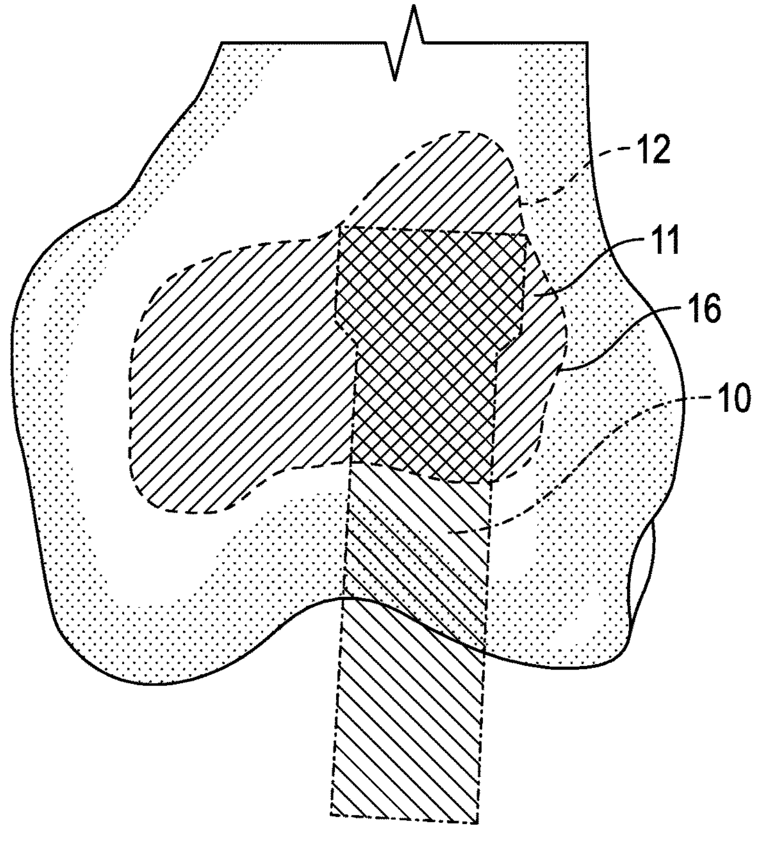
FIG. 6 illustrates a virtual representation of a custom haptic boundary based on intersecting a plane with the bone model.

During the implant planning stage, a surgeon or medical professional may use planning software associated with CAS system 200 to plan the placement of prosthetic implants onto or within a patient's anatomy. As such, virtual (i.e., software) 3-D models of prosthetic implants, the patient's anatomy, a surgical instrument (such as cutting tool(s)), and any other physical object that may be used during the surgical procedure may be generated and registered to a virtual coordinate space (generally one that corresponds with the patient's anatomy). Using planning software, the surgeon can virtually position a prosthetic implant relative to the patient's anatomy. Based on the virtual prosthetic implant model, the planning software may generate a standard haptic boundary 12. As depicted in FIG. 5, the standard haptic boundary 12 may be configured to accommodate the cutting profile and size of a cutting tool, shown schematically as cutting tool 10. However, as shown, the standard haptic boundary 12 based on the virtual implant model may under-resect or over-resect the actual bone area 11 necessary for resection to receive the implant. Over-resection risks damaging soft tissue, such as collateral ligaments in the knee joint, while under-resecting may leave unresected bone that might require snapping or cracking off and/or manual trimming off with a rongeur. A haptic boundary 12 that is tied to the boundary 16 of the intersection 11 of a reference plane of the implant model on the bone model, though, may be unable to accommodate the size and shape of the cutting tool 10 in some areas, as depicted in FIG. 6. A cutting tool, such as an oscillating saw blade, has a wide effective shape that will not likely fit into the irregular geometry of the custom haptic perimeter shown in FIG. 6.

Figure 7:
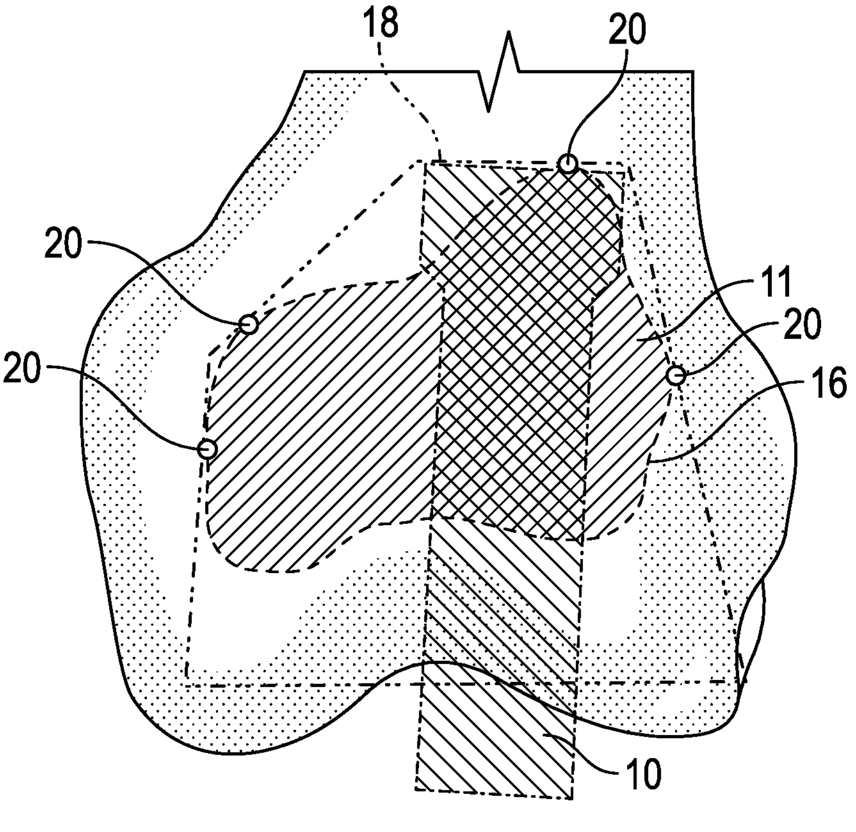
FIG. 7 illustrates a virtual representation of a customized haptic boundary in accordance with certain disclosed embodiments.

FIG. 7 depicts a customized haptic boundary 18 that is based on the configuration of the standard haptic boundary 12, and that also accommodates certain anatomic features 20 at the perimeter 16 of the intersection 11 of the patient bone and an implant reference surface. The customized haptic boundary 18 can therefore accommodate the cutting tool 10, and also more closely matches the necessary areas for bone removal to minimize under-resecting or over-resecting the bone. The generation of the customized haptic boundary 18 is described in detail with respect to the descriptions of FIGS. 8-14 below.

Figure 8:
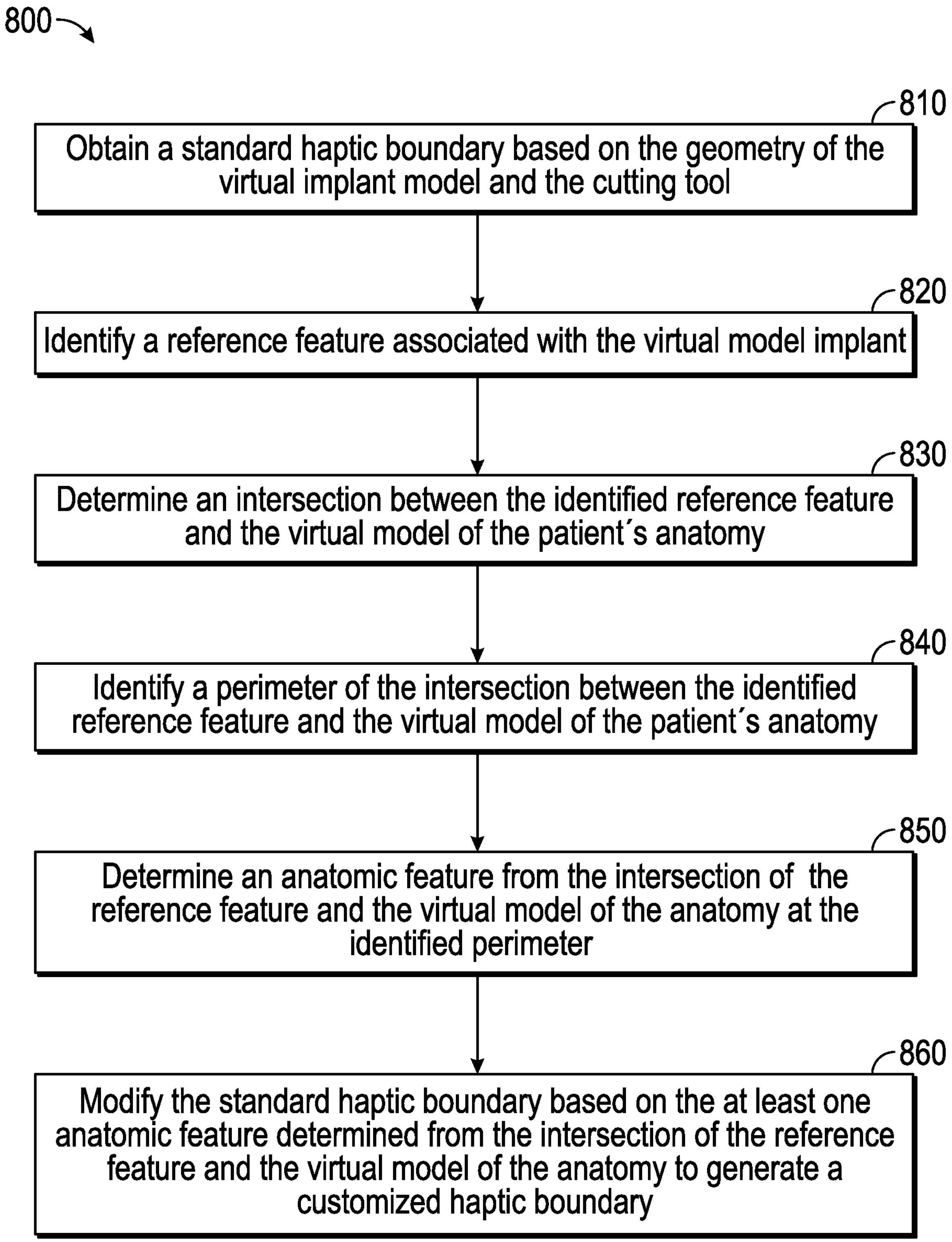
FIG. 8 provides a flowchart illustrating an exemplary method for generating customized haptic boundaries based on patient-specific anatomic data.
Figure 9:
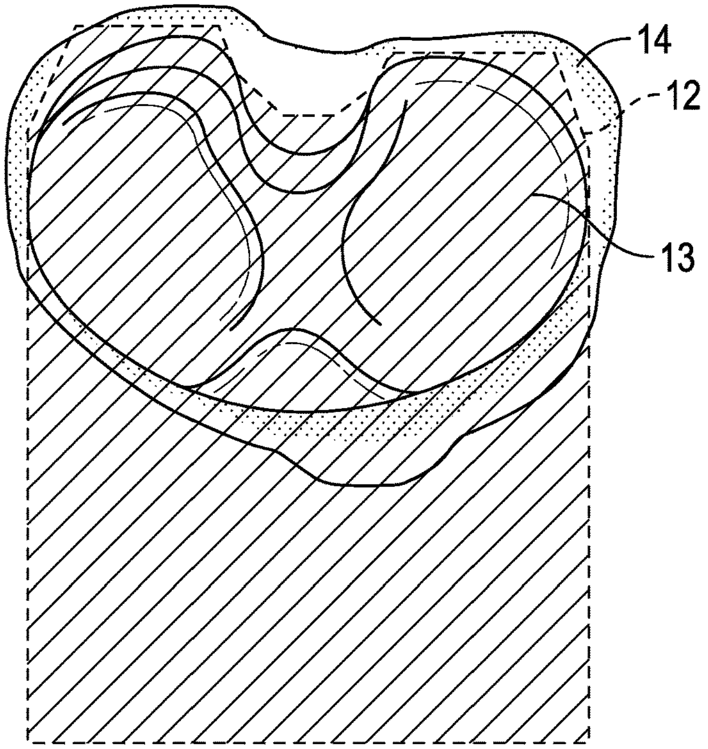
FIG. 9 illustrates a virtual representation of a step of generating a customized haptic boundary in accordance with certain disclosed embodiments.

FIG. 8 provides a flowchart 800 that illustrates an exemplary method for automatically generating a patient-specific virtual haptic boundary. According to one embodiment, the method illustrated in FIG. 8 may be implemented during an implant placement planning stage associated with the performance of a surgical procedure. The planning stage may be performed pre-operatively by a surgeon or other medical professional, prior to commencement of the surgical procedure. Alternatively or additionally, the planning stage may be performed (or repeated) intra-operatively, during the medical procedure.

As illustrated in flowchart 800 of FIG. 8, once the virtual implant model has been placed in a desired position relative to the patient's anatomy, the method commences by identifying a standard haptic boundary 12 based on the size and shape of the implant model 13 associated with the implant being used, the shape of the cutting tool, and the approach angle of the cutting tool (step 810). This standard haptic boundary 12 typically corresponds closely with the geometric shape of the prosthetic implant. According to one embodiment, however, it may differ slightly from the geometry of the implant. For example, the standard haptic boundary may be slightly larger than the prosthetic implant to allow sufficient space for surgical tool 10 access (e.g., to accommodate for the width of a cutting tool) or to provide an area for entering the volume defined by the virtual haptic boundary. The standard haptic boundary 12 is preferably a pre-determined haptic tied to the implant model, requiring no new haptic generation. A standard haptic boundary 12 is shown in relation to a virtual model of the anatomy, such as virtual bone model 14 of the proximal end of the tibia in FIG. 9.

Figure 10:
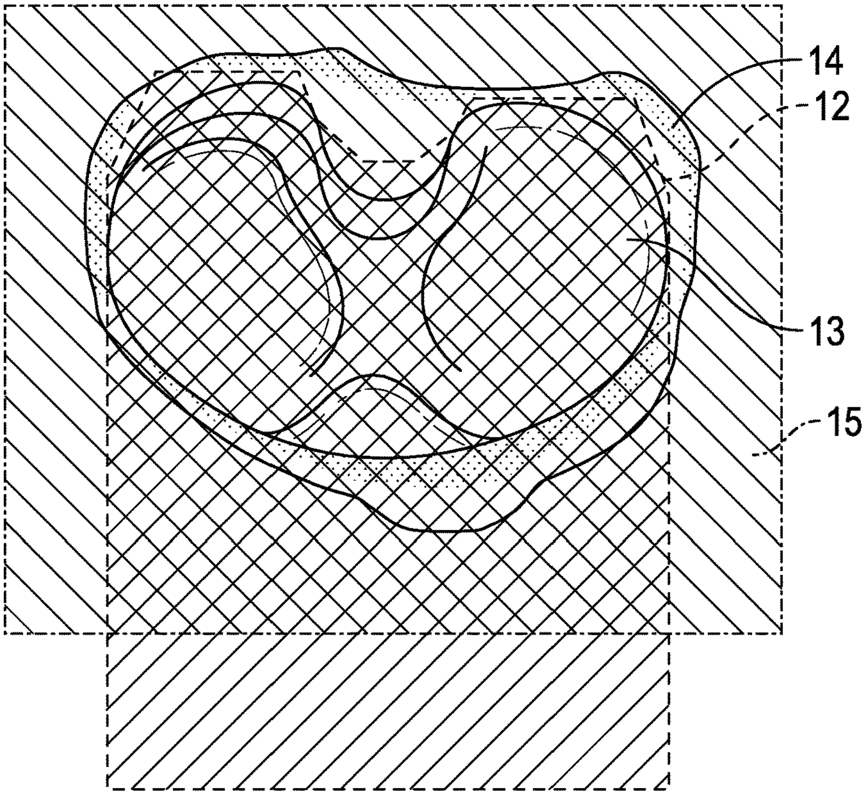
FIG. 10 illustrates a virtual representation of another step of generating a customized haptic boundary in accordance with certain disclosed embodiments.

Once the standard haptic boundary 12 is identified, the position and orientation of a reference feature 15 associated with the virtual implant model in the virtual coordinate space is identified (step 820). The reference feature 15 of the virtual implant model may embody one or more points, lines, planes, or surfaces of the virtual implant model and, by extension, the prosthetic model associated therewith. The reference feature 15 may be a reference plane a top, bottom, or other surface of the implant model, or plane that is otherwise associated with the implant model. In the embodiment of FIG. 10, the reference feature 15 is a plane shown relative to the virtual bone model 14. Alternatively or additionally, the reference feature 15 may include or embody any feature associated with the implant that the surgeon wishes to use as the reference with which to customize virtual haptic boundaries.

Figure 11:
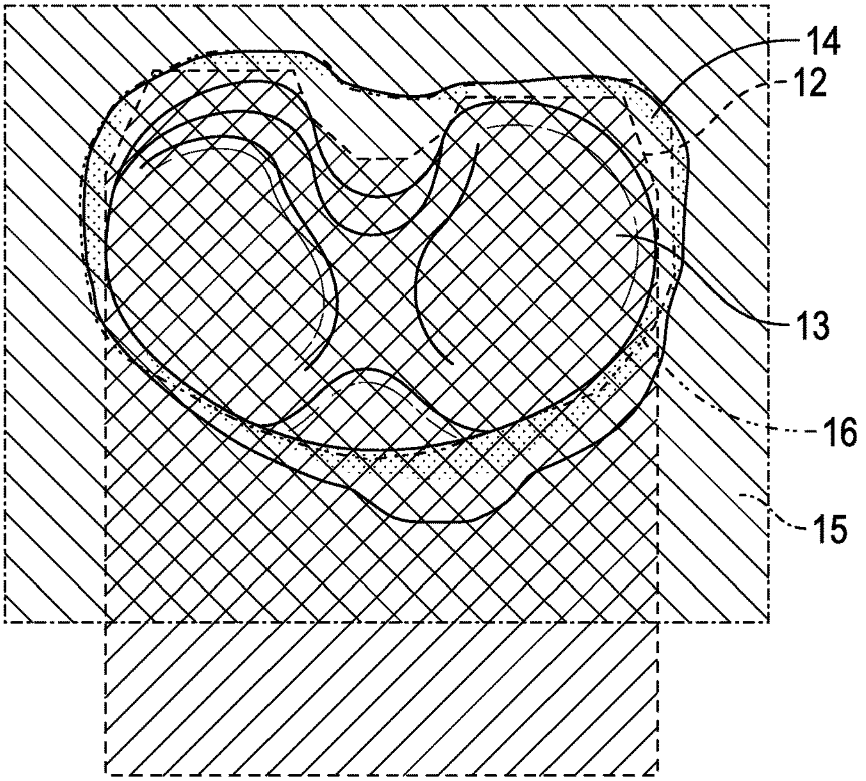
FIG. 11 illustrates a virtual representation of another step of generating a customized haptic boundary in accordance with certain disclosed embodiments.

Once the reference feature 15 associated with the virtual implant model 13 has been established, an intersection between the identified reference feature 15 and virtual model 14 of the patient's anatomy may be determined (step 830). The intersection between the reference feature 15 and the virtual model 14 of the patient's anatomy identifies a patient-specific anatomic perimeter 16 (step 840), as shown in FIG. 11.

Figure 12:
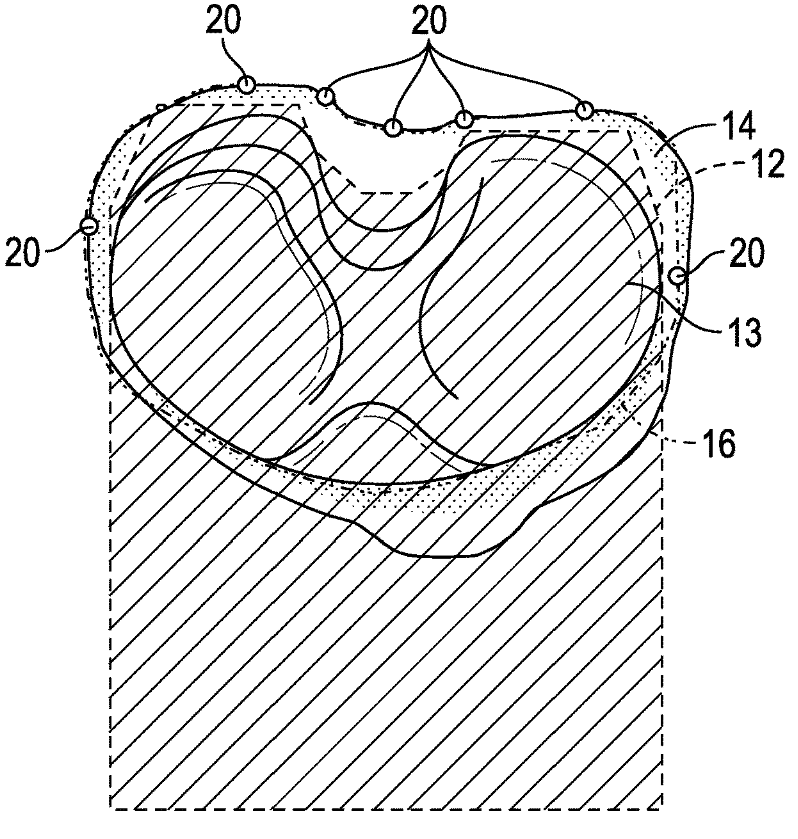
FIG. 12 illustrates a virtual representation of another step of generating a customized haptic boundary in accordance with certain disclosed embodiments.

Upon determining the anatomic perimeter 16, planning software associated with CAS system 200 may be configured to identify certain features that are specific to the patient's anatomy (step 850). As shown in FIG. 12, the anatomic features 20 are identified on the anatomic perimeter 16. The anatomic features 20 may include, for example, a most medial landmark, most posterior-medial landmark, most posterior-lateral landmark, and most lateral landmark.

As an alternative or in addition to automatic detection, information indicative of anatomic features 20, including a modification to the identified anatomic features, may be received based on a user input. For example, a surgeon may designate one or more points, lines, or areas of the patient's anatomy as anatomic landmarks manually by physically touching the points, lines, or areas of the patient's anatomy using a probe tool that has been registered with the virtual coordinate space. According to another embodiment, a user of CAS system 200 may input information associated with anatomic landmarks using a graphical user interface associated with planning software. Specifically, a user may select, via a graphical user interface, one or more points, lines, surfaces, or areas on a virtual model 14 of the patient's anatomy, or on the anatomic perimeter 16, using a mouse or other input device. For example, protruding osteophytes on the patient anatomy may unintentionally create computer generated landmarks outside of the desired cutting region. The surgeon could then deselect this landmark using a navigated probe tool or by deselecting the landmark on a virtual model using a graphical user interface.

Figure 13:
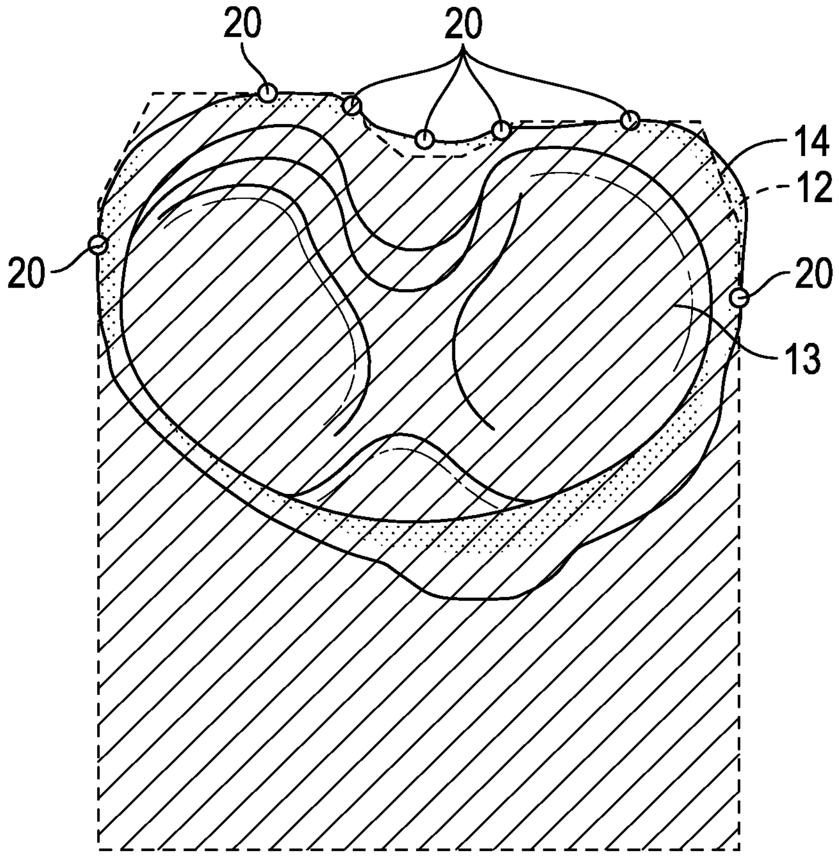
FIG. 13 illustrates a virtual representation of another step of generating a customized haptic boundary in accordance with certain disclosed embodiments.

As depicted in FIG. 13, once the anatomic features 20 are identified on the virtual model 14 of the anatomy and/or the anatomic perimeter 16, planning software associated with the CAS system 200 may be configured to modify the standard haptic boundary 12 based on the anatomic features 20 (step 860). The standard haptic boundary 12 may be stretched or shrunk to more closely match the anatomic perimeter 16. In certain embodiments, only the edges of the standard haptic boundary 12 can be moved based on simple formula percentages. Also the particular geometry can be locked if necessary to prevent disfiguration of the implant shape. In other exemplary embodiments, the standard haptic perimeter 12 may be composed of a series of simples lines or edges made up of vertexes. Each vertex may be designated to stretch in only certain directions, to not stretch (i.e. remain fixed), or to not stretch more than a specified amount. For example, the medial edge vertexes of a standard haptic boundary 12 for a tibial component can be designated to only move/stretch medial-lateral and to move/stretch together as a group, so as to maintain the basic shape. Control of the adaptability of the vertexes helps to ensure that the customized haptic boundary 18 maintains a shape that can accommodate the cutting tool 10.

Alternatively or additionally, the step of modifying the haptic boundary 12 may be performed as a manual process by a surgeon. For example, after the anatomic perimeter 16 has been identified and/or the anatomic features 20 have been determined (either automatically by the planning software or manually by the surgeon), the surgeon may modify the standard virtual haptic boundary 12 that was previously established, or the automatically established customized haptic boundary 18. In particular, a surgeon may input information associated with moving the haptic boundary using a graphical user interface associated with planning software. For example, a surgeon may wish to contract the inner edges of virtual haptic boundaries associated with a tibial component base portion to limit the operation of the cutting tool near the tibial eminence, and avoid the possibility of inadvertently damaging soft tissues (e.g., ACL or PCL) that attach thereto. To do so, the surgeon may select, via a graphical user interface, one or more boundaries or vertexes of the haptic boundary and apply a manipulation to stretch/move the boundary, using a mouse or other input device.

In one embodiment, the surgeon sets a series of offset preferences for the stretchable boundaries. For example, the surgeon may desire that the haptic boundary be offset outwardly from the anatomic landmark by a set distance to enable the cutting tool to cut outside the bone perimeter for improved cutting efficiency. Conversely, the surgeon may desire to set the haptic boundary offset inwardly from the anatomic landmark by a set distance to conservatively protect soft tissues.

Once generated, the customized haptic boundary may be registered to the patient's anatomy and displayed on display of CAS system 200. Specifically, when the customized virtual haptic boundary 18 is generated, planning software associated with CAS system 200 may be configured to map the virtual surfaces and features that define the customized virtual haptic boundary 18 to the virtual coordinate space associated with the patient's anatomy. As such, the boundary surfaces associated with the customized virtual haptic boundary 18 become linked to the patient's anatomy, thereby defining the areas of the patient's anatomy within which the surgical instrument is permitted to operate. By registering the customized virtual haptic boundary 18 to the patient's anatomy, the customized virtual haptic boundary 18 becomes virtually linked to the patient's anatomy, so that the customized virtual haptic boundary 18 can be tracked (and viewed) relative to the specific movements, modifications, and adjustments in the patient's anatomy during the surgical procedure. CAS system 200 may then apply the virtual haptic boundary to surgical instrument.

Figure 14:
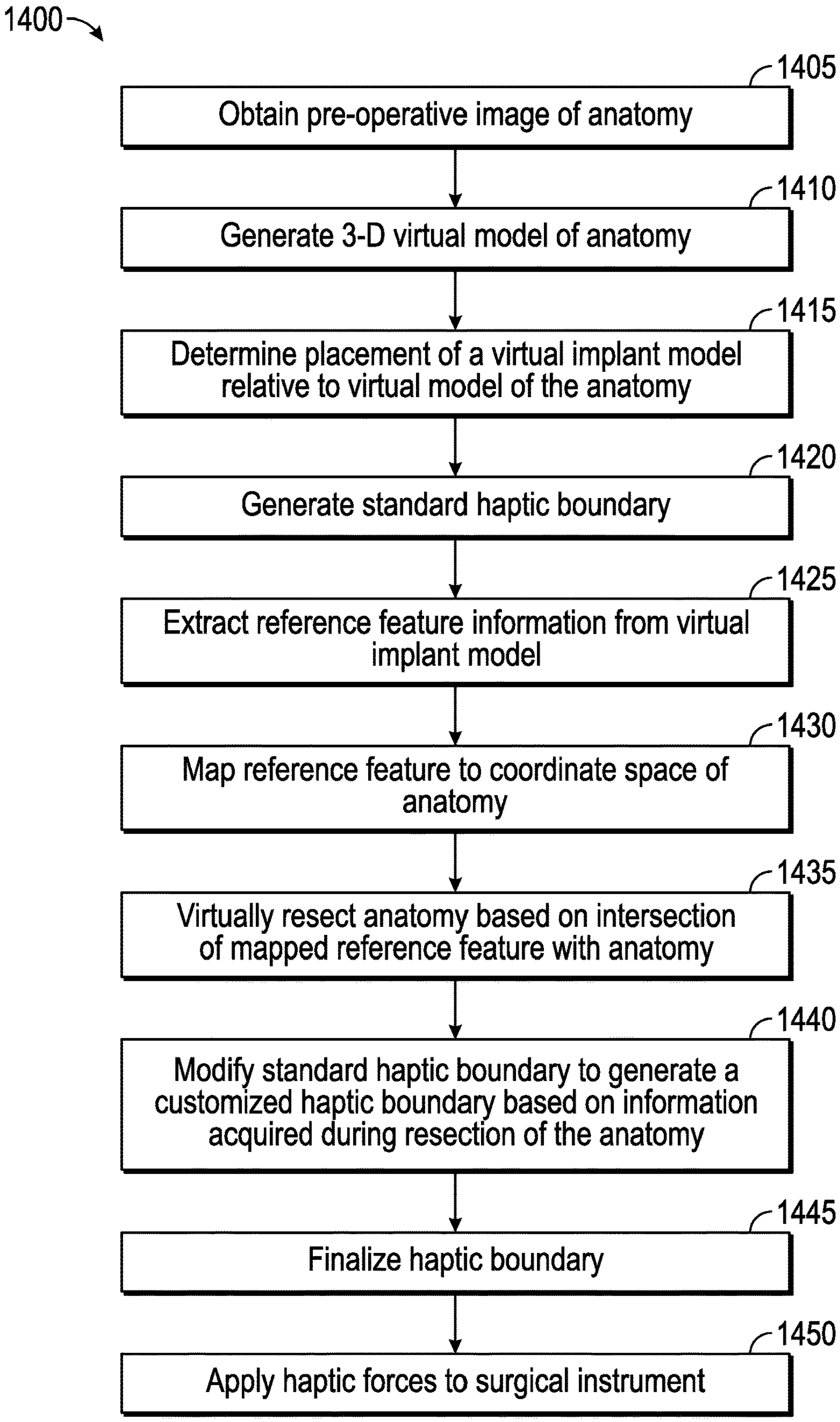
FIG. 14 provides a flowchart illustrating another exemplary method for generating a customized haptic boundary based on patient-specific anatomic data.

FIG. 14 provides a flowchart showing another exemplary method 1400 for customizing a haptic boundary based on patient-specific parameters. As illustrated in FIG. 14, the method commences upon receipt of pre-operative image(s) or image data associated with a patient's anatomy (step 1405). Pre-operative image(s) may include any two- or three-dimensional image data set obtained using any suitable imaging process for recording images associated with a patient's anatomy such as, for example, x-ray, computed tomography (CT), magnetic resonance (MR), positron emission tomography (PET), single photon emission computed tomography (SPECT), ultrasound, etc. According to one embodiment, I/O devices 236 of CAS system 200 may receive pre-operative CT scan data 260 associated with the anatomy of the specific patient that is to be operated on.

Upon receiving pre-operative image of the anatomy of a patient, software associated with CAS system 200 generates a 3-D virtual model of the patient's anatomy (step 1410). For example, CAS system 200 may include one of a number of different software tools for rendering 3-D models of objects, based on the received 2-D (or 3-D) image data sets associated with the anatomy of the patient. In an alternative embodiment, the 3-D virtual model of the patient's anatomy is generated utilizing an imageless system.

After the virtual model 14 of the patient's anatomy is generated, it may be registered with the actual anatomy of the patient so that CAS system 200 can virtually track the position and orientation of the actual anatomy of the patient in virtual software space. According to one embodiment, this registration process involves associating a plurality of points of the patient's anatomy with corresponding points on the virtual model. Such associations can be made using a probe tool that has been registered in the virtual coordinate space, whereby a plurality of points on the patient's anatomy gathered by touching or "exploring" one or more surfaces of the patient's anatomy using the tip of the probe tool. Once the virtual model 14 is registered with the patient's anatomy, CAS system 200 may be able to track the position and orientation of the patient's anatomy in the virtual coordinate space.

After the 3-D virtual model 14 of the patient's anatomy is generated and registered to the patient's bone, planning software of CAS system 200 facilitates the planning of an prosthetic implant within the patient's anatomy (step 1415). Specifically, planning software of CAS system 200 determines, based on a user input, placement of a virtual implant model 13 relative to the virtual model 14 of the patient's anatomy. For example, a surgeon may select a virtual implant model 13 (e.g., virtual model associated with tibial base portion 121 as shown in FIG. 4) from a database of implants available for the surgery. Using a graphical user interface 400, the surgeon may manipulate the position of the virtual implant model 13 relative to the patient's anatomy (e.g., tibia 101), which produces a virtual representation of the tibia fitted with the virtual implant, as shown in the lower left sub-screen of graphical user interface 400 of FIG. 4. Such a process for virtually planning implant placement allows the surgeon to make precise adjustments to the position of the implant relative to the patient's anatomy in a simulated software environment, prior to commencing the bone resection process.

Once the placement of the virtual implant model 13 with respect to the virtual model 14 of the patient's anatomy is finalized, a standard haptic boundary 12 is generated (step 1420). The standard haptic boundary 12 may correspond closely with the geometric shape of the prosthetic implant. Reference feature 15 information is extracted from the virtual implant model 13 (step 1425). According to one embodiment, the reference feature 15 of the virtual implant model may embody one or more points, lines, planes, or surfaces of the virtual implant model 13. As illustrated in the embodiments described above, the reference feature 15 is a plane associated with the implant model 13. Alternatively or additionally, the reference feature 15 may include or embody any feature associated with the implant that the surgeon wishes to use as the reference with which to customize virtual haptic boundaries. For example, reference feature 15 may include any surface associated with the virtual implant model 13 that directly abuts or faces a surface of the virtual model 14 associated with the patient's anatomy.

Upon extracting the reference feature information, planning software associated with CAS system 200 maps the reference feature information onto the coordinate space of the patient's anatomy (step 1430). That is, planning software associated with CAS system 200 registers the reference features 15 of the virtual implant model 13 to the virtual model 14 of the patient's bone, such that the reference surfaces 15 are tracked relative to the position of the patient's bone.

Further referring to FIG. 14, planning software of CAS system 200 determines the intersection between the mapped reference surface 15 and the patient's anatomy 14, and virtually resects tissue based on the determined intersection (step 1435). Planning software of CAS system 200 may also be configured to modify the standard haptic boundary 12 to generate a customized haptic boundary 18 (step 1440) based on information acquired during resection of the anatomy. As described above, the customized haptic boundary 18 may be generated by stretching/moving the standard haptic boundary 12 based upon at least one anatomic feature 20 located on an anatomic perimeter 16, which is defined by the intersection of the reference surface 15 and the patient's anatomy 14. The identification of the anatomic features 20 may be done automatically by the CAS system 200 or may be performed manually by the surgeon. Similarly, the modification of the standard haptic boundary 12 may be performed automatically based on the previously identified anatomic features 20, or may be performed manually by the surgeon who moves/stretches the boundary based on the patient specific anatomy or according to desired cutting approaches and techniques, i.e. to limit the operation of the cutting tool near the tibial eminence, and avoid the possibility of inadvertently damaging soft tissues (e.g., ACL or PCL) that attach thereto.

Upon generating the customized virtual haptic boundary 18, planning software of CAS system 200 provides the user with an option to finalize the virtual haptic boundary (step 1445). When the user decides to finalize the virtual haptic boundary, CAS system 200 may update the force system with the coordinates of virtual haptic boundary. As such, CAS system 200 selectively applies the virtual haptic forces to surgical instrument based on the tracked position of the surgical instrument relative to the virtual haptic boundary (step 1450).

The presently disclosed systems and methods for customizing virtual haptic boundaries provide a solution for adjusting virtual haptic boundaries associated with force feedback control system for computer-assisted surgery systems. According to one embodiment, this solution allows a user to modify a haptic boundary by stretching or contracting an existing haptic boundary to fit one or more anatomic landmarks. The planning software may then determine an intersection between the stretched (or contracted) boundary and the virtual model of the patient's anatomy to define the location of the new virtual haptic boundary, and establish the new virtual haptic boundary based on the determined intersection.

The foregoing descriptions have been presented for purposes of illustration and description. They are not exhaustive and do not limit the disclosed embodiments to the precise form disclosed. Modifications and variations are possible in light of the above teachings or may be acquired from practicing the disclosed embodiments. For example, the described implementation includes software, but the disclosed embodiments may be implemented as a combination of hardware and software or in firmware. Examples of hardware include computing or processing systems, including personal computers, servers, laptops, mainframes, microprocessors, and the like. Additionally, although disclosed aspects are described as being stored in a memory, one skilled in the art will appreciate that these aspects can also be stored on other types of computer-readable storage devices, such as secondary storage devices, like hard disks, floppy disks, a CD-ROM, USB media, DVD, or other forms of RAM or ROM.

It will be apparent to those skilled in the art that various modifications and variations can be made to the disclosed systems and associated methods for customizing interactive haptic boundaries based on patient-specific data. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A method, comprising:

providing, based on a planned implant position, a boundary defining a portion of a bone to be resected;

determining a position of a tracked probe;

obtaining a customized boundary by changing a shape of the boundary based on the position of the tracked probe without affecting the planned implant position; and guiding operation of a cutting tool in an area defined by the customized boundary.

2. The method of claim 1, comprising displaying the boundary relative to a virtual representation of the bone, wherein changing the shape of the boundary comprises allowing a user to select and move a vertex of the control boundary using an input device.

3. The method of claim 2, comprising generating the virtual representation of the bone based on imaging of the bone.

4. The method of claim 1, wherein providing the boundary comprises obtaining the boundary from a library of standard boundaries.

5. The method of claim 1, wherein the position of the tracked probe indicates a position on an anatomic structure of a patient.

6. The method of claim 1, further comprising selecting an implant component to be implanted on the bone and providing the boundary based on the implant component.

7. The method of claim 1, wherein the position of the tracked probe indicates a position of a soft tissue.

8. The method of claim 1, wherein guiding the operation of the cutting tool comprises providing feedback to a user based on a position of the cutting tool relative to the customized boundary.

9. A method, comprising:

providing, based on a planned implant position, a boundary defining a portion of a bone to be resected;

obtaining a customized boundary by changing the boundary based on a position of a patient tissue without affecting the planned implant position; and guiding a bone resection based on the customized boundary.

10. The method of claim 9, wherein providing the boundary comprises loading the boundary from computer memory, wherein the boundary is a standard boundary associated with an implant planned to be implanted in the planned implant position.

11. The method of claim 9, wherein providing the boundary comprises selecting the boundary based on selection of an implant such that the boundary is a predefined boundary associated with the implant.

12. The method of claim 9, comprising determining the position of the patient tissue by tracking a probe.

13. The method of claim 12, wherein the patient tissue is a soft tissue.

14. The method of claim 9, wherein guiding operation of the surgical tool based on the customized boundary comprises causing the surgical tool to operate on the bone inside the customized boundary.

15. The method of claim 9, wherein guiding operation of the surgical tool based on the customized boundary comprises controlling a robotic device interfacing with the surgical tool.

16. A system, comprising:

a tracked probe;

an optical tracking system configured to track the tracked probe; and one or more non-transitory computer-readable media storing programming instructions that, when executed by one or more processors, cause the one or more processors to perform operations comprising:

providing, based on a planned implant position, a boundary defining a portion of a bone to be resected;

determining a position of the tracked probe;

obtaining a customized boundary by changing a shape of the boundary based on the position of the tracked probe without affecting the planned implant position; and guiding operation of a cutting tool in an area defined by the customized boundary.

17. The system of claim 16, further comprising a robotic arm, wherein guiding operation of the cutting tool comprises controlling the robotic arm based on the customized boundary.

18. The system of claim 16, wherein providing the boundary comprises loading the boundary from storage in the one or more non-transitory computer-readable media.

19. The system of claim 16, wherein the boundary corresponds to a shape of an implant for implantation at the bone.

20. The system of claim 16, wherein obtaining the customized boundary by changing the shape of the boundary based on the position of the tracked probe comprises registering a position of a patient tissue based on the position of the tracked probe and changing the shape of the boundary based on the position of the patient tissue.

* * * * *